(12) United States Patent
Ishiguro

(10) Patent No.: US 11,975,191 B2
(45) Date of Patent: May 7, 2024

(54) STRETCHABLE WIRING BOARD AND ELECTRICAL MUSCLE STIMULATING DEVICE

(71) Applicant: NIPPON MEKTRON, LTD., Tokyo (JP)

(72) Inventor: Toshihide Ishiguro, Tokyo (JP)

(73) Assignee: NIPPON MEKTRON, LTD., Tokyo (JP)

( * ) Notice: Subject to any disclaimer, the term of this patent is extended or adjusted under 35 U.S.C. 154(b) by 1043 days.

(21) Appl. No.: 16/863,100

(22) Filed: Apr. 30, 2020

(65) Prior Publication Data

US 2021/0046309 A1 Feb. 18, 2021

(30) Foreign Application Priority Data

Aug. 13, 2019 (JP) ................... 2019-148453

(51) Int. Cl.
| | |
|---|---|
| *A61N 1/36* | (2006.01) |
| *A61B 5/395* | (2021.01) |
| *A61N 1/04* | (2006.01) |
| *A61N 1/375* | (2006.01) |
| *H05K 1/02* | (2006.01) |
| *H05K 1/09* | (2006.01) |

(52) U.S. Cl.
CPC .......... *A61N 1/36003* (2013.01); *A61B 5/395* (2021.01); *A61N 1/0452* (2013.01); *A61N 1/0492* (2013.01); *A61N 1/3752* (2013.01); *H05K 1/0265* (2013.01); *H05K 1/0283* (2013.01); *H05K 1/09* (2013.01)

(58) Field of Classification Search
CPC ............................ A61B 5/395; A61N 1/36003

USPC ......................................................... 607/152
See application file for complete search history.

(56) References Cited

U.S. PATENT DOCUMENTS

| | | | |
|---|---|---|---|
| 9,847,171 | B2 | 12/2017 | Kato |
| 2016/0049240 | A1 | 2/2016 | Kato |

FOREIGN PATENT DOCUMENTS

| | | | | |
|---|---|---|---|---|
| JP | 2009-112632 | A | 5/2009 | |
| JP | 2017-143257 | A | 8/2017 | |
| JP | 2018-107209 | A | 7/2018 | |
| JP | 2018-174054 | A | 11/2018 | |
| JP | 2019-054942 | A | 4/2019 | |
| WO | WO-2007006633 | A1 * | 1/2007 | ................ C09J 9/02 |
| WO | 2014/203633 | A1 | 12/2014 | |

OTHER PUBLICATIONS

An Office Action; "Notice of Reasons for Refusal," mailed by the Japanese Patent Office on Apr. 4, 2023, which corresponds to Japanese Patent Application No. 2019-148453 and is related to U.S. Appl. No. 16/863,100; with English language translation.

\* cited by examiner

*Primary Examiner* — Nadia A Mahmood

(74) *Attorney, Agent, or Firm* — Studebaker & Brackett PC

(57) ABSTRACT

Provided is a stretchable wiring board including: a base material having stretchability; a wiring line having at least a portion coated and formed on the base material with a conductive stretchable material; and an uneven engaging portion that is electrically connected to the wiring line and has a protrusion or a recess configured to engage with a connection terminal of an external device.

12 Claims, 12 Drawing Sheets

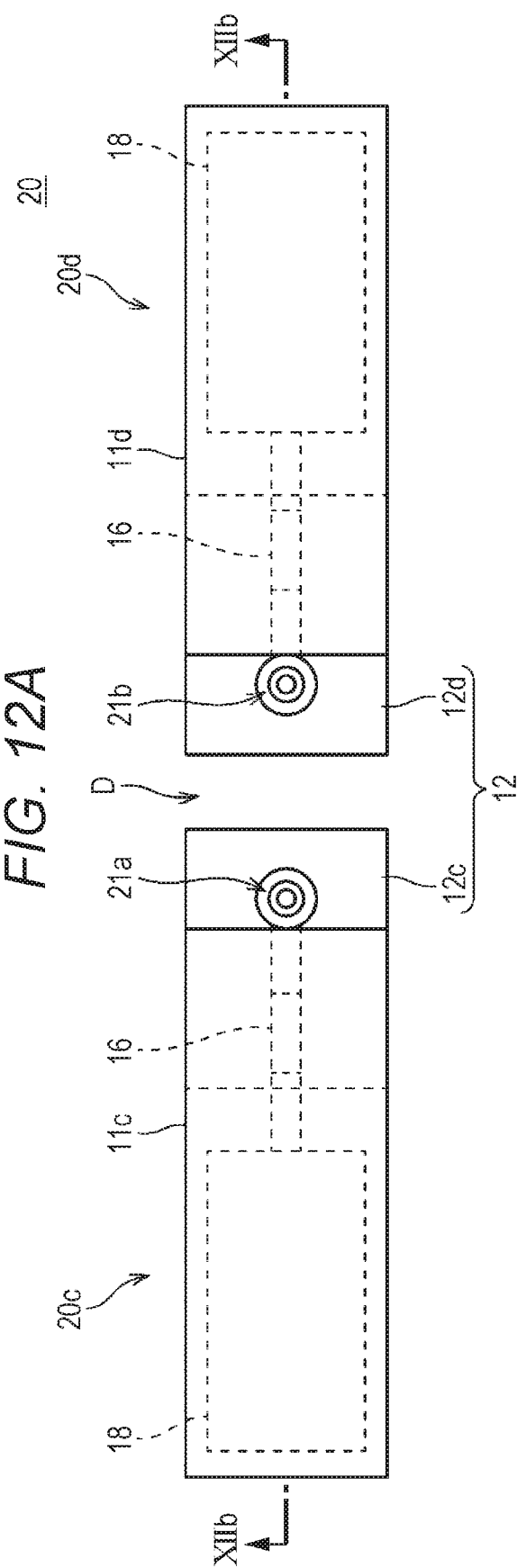
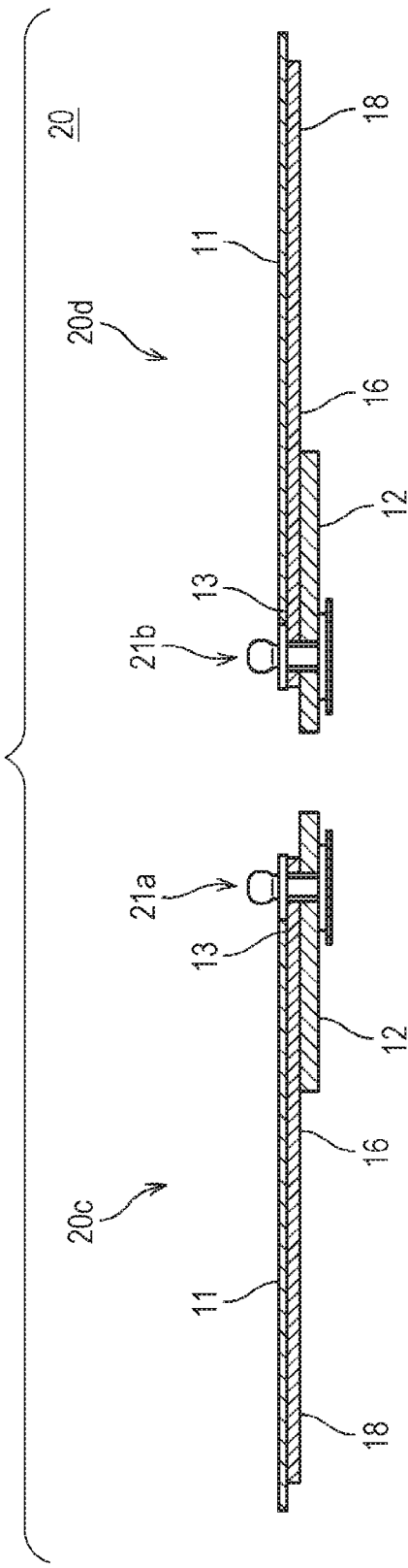
FIG. 12A
FIG. 12B

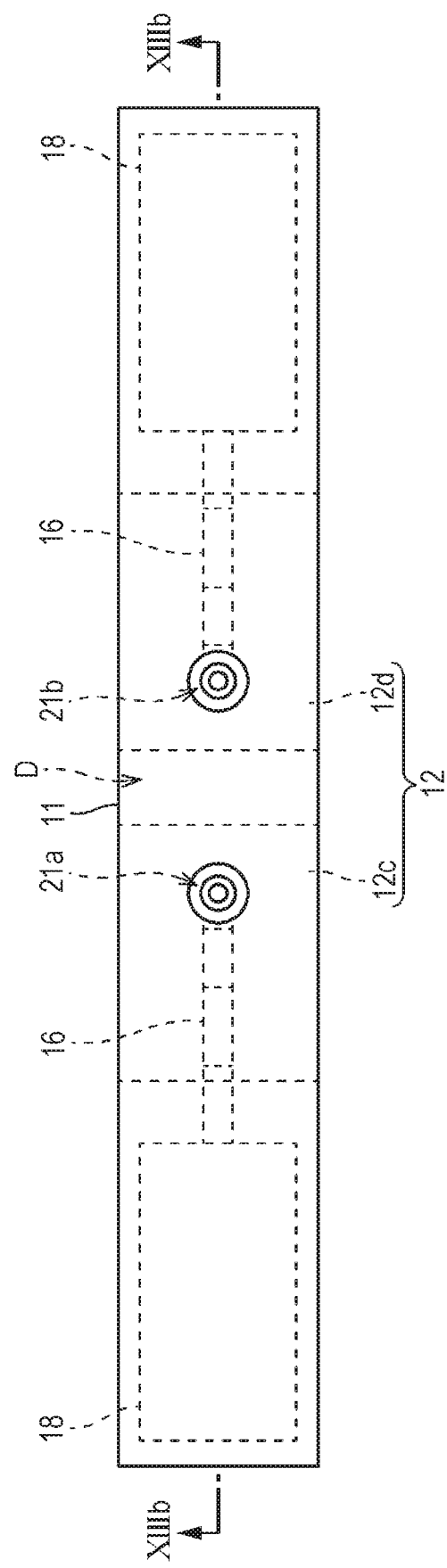
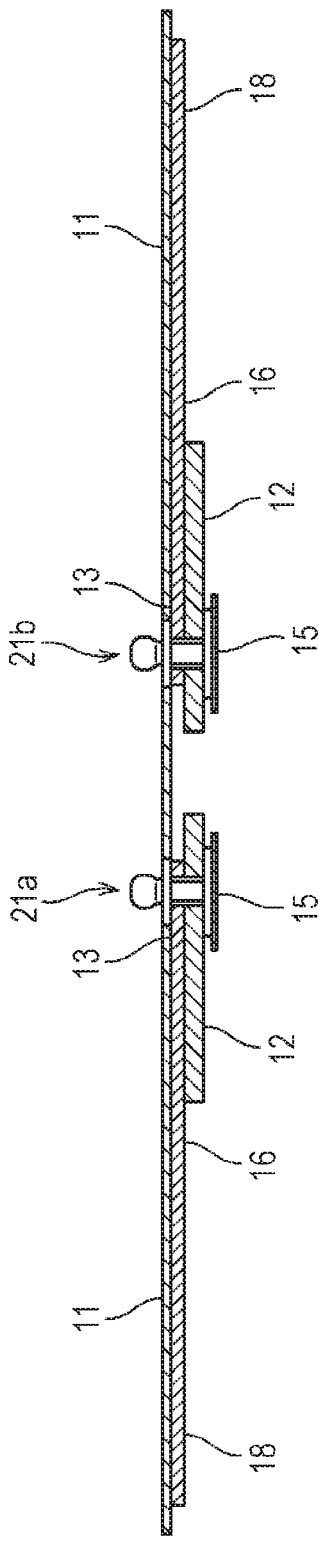

STRETCHABLE WIRING BOARD AND ELECTRICAL MUSCLE STIMULATING DEVICE

CROSS-REFERENCE TO RELATED APPLICATION

This application claims priority from Japanese Patent Application No. 2019-148453 filed with the Japan Patent Office on Aug. 13, 2019, the entire content of which is hereby incorporated by reference.

BACKGROUND

1. Technical Field

The present disclosure relates to a stretchable wiring board and an electrical muscle stimulating device.

2. Related Art

A device for EMS (Electrical Muscle Stimulation) exercise, which applies electrical stimulation to muscles using electrodes in contact with a skin of a living body, has been put to practical use. Such a device is described in, for example, JP-A-2019-054942. An electrical muscle stimulating device (hereinafter also referred to as an EMS device) described in JP-A-2019-054942 is provided with a plurality of flexible bending pieces having a plurality of electrodes for applying electrical stimulation to the living body. A function of accommodating a controller is provided at the center of the plurality of bending pieces. Electric power is supplied to each electrode from the controller. Conductive sheet-like gel bodies are arranged on the electrodes in an overlapping manner. The electrodes are attached to the skin of the living body by the gel bodies. Thus, the electrical muscle stimulating device is attached to a body.

When adhesion between the skin and the electrodes is low, the stimulation provided by the electrodes may be too strong. In this case, the living body feels pain. Further, when the living body wearing the electrical muscle stimulating device takes exercise or the like, the electrical muscle stimulating device may come off the body. In order to solve this problem, some electrical muscle stimulating devices are being studied so that the adhesion of the bending pieces and the electrodes to the skin is improved, and the electrical muscle stimulating device expands and contracts following movement of the body.

JP-A-2018-107209 describes a stretchable wiring board having high adhesiveness to the skin and high followability to the movement of the body. The stretchable wiring board includes a stretchable base material having stretchability, an external terminal formed on the stretchable base material, and a wiring line connecting the external terminal and a terminal for taking an electrical signal.

SUMMARY

A stretchable wiring board according to an embodiment of the present disclosure includes: a base material having stretchability; a wiring line having at least a portion coated and formed on the base material with a conductive stretchable material; and an uneven engaging portion that is electrically connected to the wiring line and has a protrusion or a recess configured to engage with a connection terminal of an external device.

BRIEF DESCRIPTION OF THE DRAWINGS

FIG. 12A is a top view of the stretchable wiring board according to a second embodiment;

FIG. 12B is an end view of the stretchable wiring board taken along a one-dot chain line illustrated in FIG. 12A;

FIG. 13A is a top view of the stretchable wiring board of a modification of the second embodiment; and FIG. 13B is an end view of the stretchable wiring board taken along a one-dot chain line illustrated in FIG. 13A.

DETAILED DESCRIPTION

Figure 1:
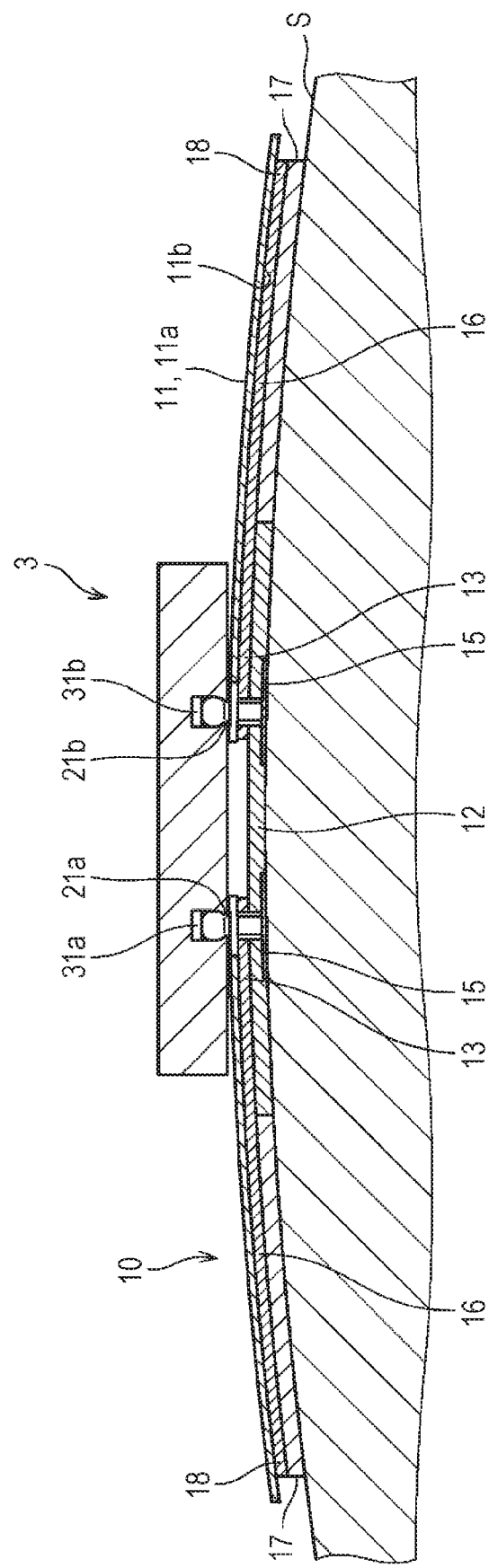
FIG. 1 is a schematic view illustrating an EMS device according to a first embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

However, the stretchable wiring board described in JP-A-2018-107209 is configured such that an external terminal can be inserted into and removed from a connector of an external device. In JP-A-2018-107209, the stretchable wiring board is formed such that a width of a film base material and a width of a stretchable base material in which the external terminal and a part of a wiring line are formed are less than the other portions of the stretchable wiring board. In this way, the external terminal held by hand can be easily inserted into and removed from the connector. Therefore, a problem of the stretchable wiring board described in JP-A-2018-107209 is that degree of freedom of wiring layout around the terminal is low.

In view of the foregoing, the present disclosure relates to a stretchable wiring board that expands and contracts following a skin of a living body and has a high degree of freedom of wiring layout, and an electrical muscle stimulating device.

A stretchable wiring board according to the present disclosure includes: a base material having stretchability; a wiring line having at least a portion coated and formed on the base material with a conductive stretchable material; and an uneven engaging portion that is electrically connected to the wiring line and has a protrusion or a recess configured to engage with a connection terminal of an external device.

An electrical muscle stimulating device according to the present disclosure includes: a stretchable wiring board including a base material having stretchability, a wiring line coated and formed on the base material with a conductive stretchable material, and an uneven engaging portion electrically connected to the wiring line and having a protrusion or a recess; and an external device including a connection terminal engaged with the protrusion or the recess of the uneven engaging portion.

According to the present disclosure, it is possible to provide the stretchable wiring board that expands and contracts following the skin of the living body and has a high degree of freedom of wiring layout, and the electrical muscle stimulating device.

Hereinafter, a first embodiment and a second embodiment of the present disclosure will be described. Drawings used in the first embodiment and the second embodiment are schematic views illustrating structure and arrangement of the stretchable wiring board and the electrical muscle stimulating device of the present disclosure, and a relationship between respective members. The drawings do not limit size and shape of the stretchable wiring board and the electrical muscle stimulating device of the present disclosure.

In the first embodiment and the second embodiment, the same members are denoted by the same reference numerals. In addition, a part of the description of the same members may be omitted.

First Embodiment (Electrical Muscle Stimulating Device)

Figure 2:
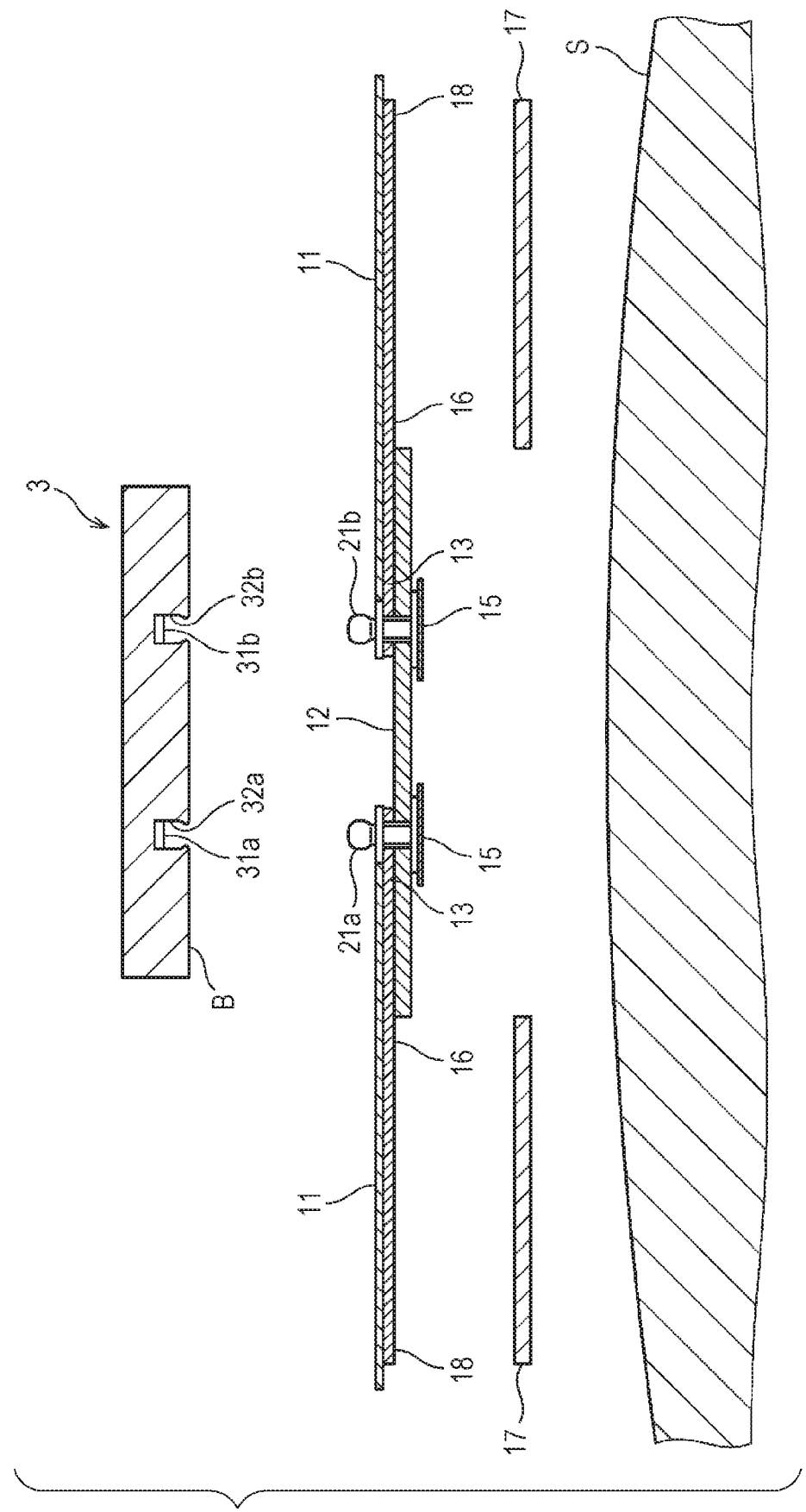
FIG. 2 is an exploded view of the EMS device illustrated in FIG. 1.

FIG. 1 is a schematic view of an end surface of an EMS device 1 illustrating the electrical muscle stimulating device according to the first embodiment. FIG. 2 is an exploded view of the EMS device 1 illustrated in FIG. 1. The EMS device is a device configured to apply electrical stimulation to a muscle of the living body to support muscle training.

The EMS device 1 includes a base material 11 having stretchability, a stretchable wiring board 10, and an external device 3. The stretchable wiring board 10 includes a wiring line 16 and conductive hooks 21a and 21b. At least a portion of the wiring line 16 is coated and formed on the base material 11 with the conductive stretchable material. The conductive hooks 21a and 21b are uneven engaging portions electrically connected with the wiring line 16 and having protrusions or recesses. The external device 3 includes connection terminals 31a and 31b engaged with the protrusions or the recesses of the conductive hooks 21a and 21b.

A wiring electrode 13 is a land electrode that is electrically connected with the conductive hooks 21a and 21b at an end of the wiring line 16. The wiring line 16 is electrically connected with the conductive hooks 21a and 21b through the wiring electrode 13. The wiring line 16 is connected to an electrode pad 18 at an end opposite to the wiring electrode 13.

When the EMS device 1 is used, the stretchable wiring board 10 is attached to a skin S of the living body. In the first embodiment, the living body is a human. The skin S is a human skin. However, an application target of the EMS device 1 is not limited to the human. The stretchable wiring board 10 can be attached to an animal body. Thus, the stretchable wiring board 10 can be used for eliminating obesity in animals or for rehabilitation for animals.

The base material 11 is a sheet-like thin film having two main surfaces. In the first embodiment, when the stretchable wiring board 10 in use is attached to the skin S, the main surface facing the skin S among the two main surfaces is defined as a lower surface 11b. On the other hand, a surface opposite to the lower surface 11b is defined as an upper surface 11a.

The EMS device 1 having the above structure further includes a non-stretchable base material 12. The non-stretchable base material 12 is disposed on the lower surface 11b side of the base material 11 and supports the base material 11.

In the structure of the EMS device 1, the external device 3 is attached to the stretchable wiring board 10. The external device 3 of the first embodiment has a substantially cubic appearance when viewed from the front. A battery that supplies power to the stretchable wiring board 10, a relay device that supplies power to the stretchable wiring board 10 from an external power source, or the like is provided inside the external device 3. Further, the external device 3 may include, for example, an operation part for adjusting a magnitude of the power supplied to the stretchable wiring board 10, frequency of the current, or timing of the power supply, and a display for displaying the operation content.

The external device 3 may be configured to include a relatively small microcomputer or the like.

The external device 3 has recesses 32a and 32b on a bottom surface B facing the skin S. When the connection terminals 31a and 31b arranged on the external device 3 and the conductive hooks 21a and 21b come into contact with each other, the power is supplied from the external device 3 to the stretchable wiring board 10.

Specifically, the conductive hooks 21a and 21b are inserted into the recesses 32a and 32b. Thus, the connection terminals 31a and 31b arranged at bottoms of the recesses 32a and 32b and the conductive hooks 21a and 21b come into contact with each other.

However, modes of the connection terminals 31a and 31b and the conductive hooks 21a and 21b are not limited to the connection terminals 31a and 31b arranged in the recesses 32a and 32b, and the conductive hooks 21a and 21b having a convex shape. The connection terminals 31a and 31b may have a convex shape. Further, the conductive hooks 21a and 21b may have a concave shape adapted to the convex shape.

The EMS device 1 is attached to the skin S with a gel layer 17 on a surface of the electrode pad 18 facing the skin S. As the gel layer 17, a member having compatibility with the living body and conductivity is used. On the side of the conductive hooks 21a and 21b facing the skin S, insulating tapes 15 are attached. The insulating tapes 15 restrain the current from flowing directly to the skin S from the conductive hooks 21a and 21b.

According to the EMS device 1 having the above structure, the current flows from the conductive hooks 21a and 21b to the wiring electrode 13. Further, the current flows to the electrode pad 18 through the wiring line 16. Thereafter, the current flows through the gel layer 17 to the skin S to stimulate the muscle. During this time, the insulating tapes 15 under the conductive hooks 21a and 21b block flow of the current to the skin S. Further, the non-stretchable base material 12 under the wiring line 16 restrains the current from being transmitted to the skin S from the wiring line 16. The current is transmitted to the skin S through the gel layer 17 only from the electrode pad 18.

[Stretchable Wiring Board]

Figure 3:
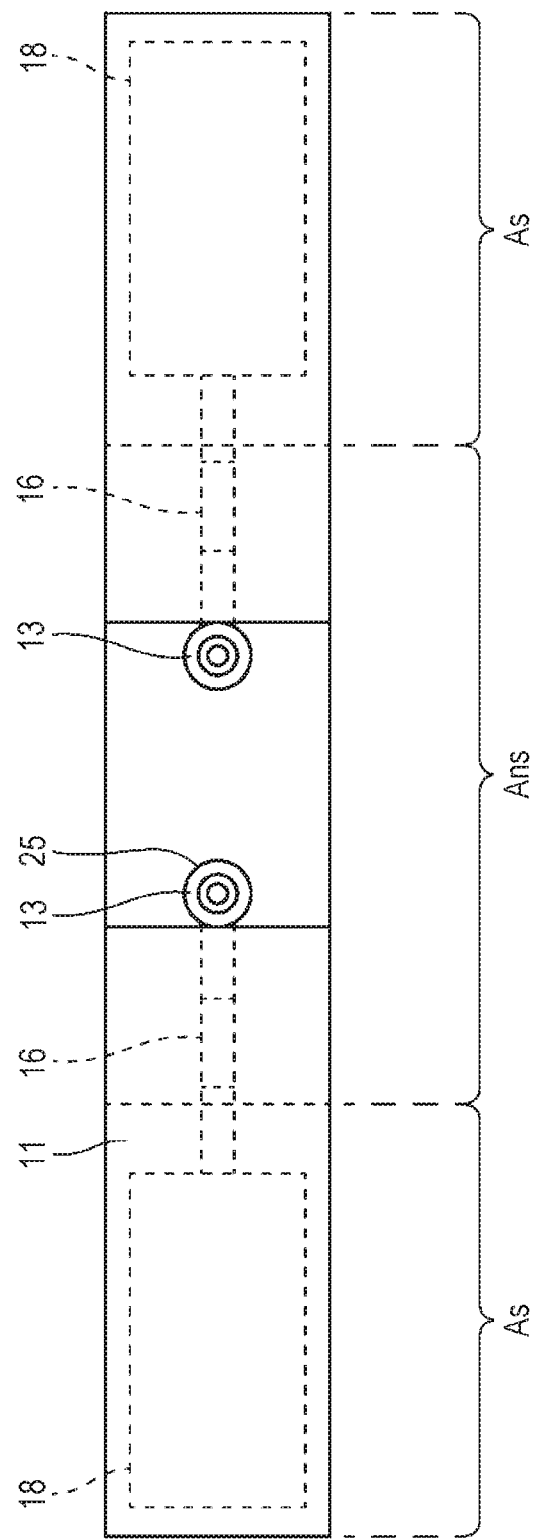
FIG. 3 is a top view of a stretchable wiring board illustrated in FIG. 1.
Figure 4:
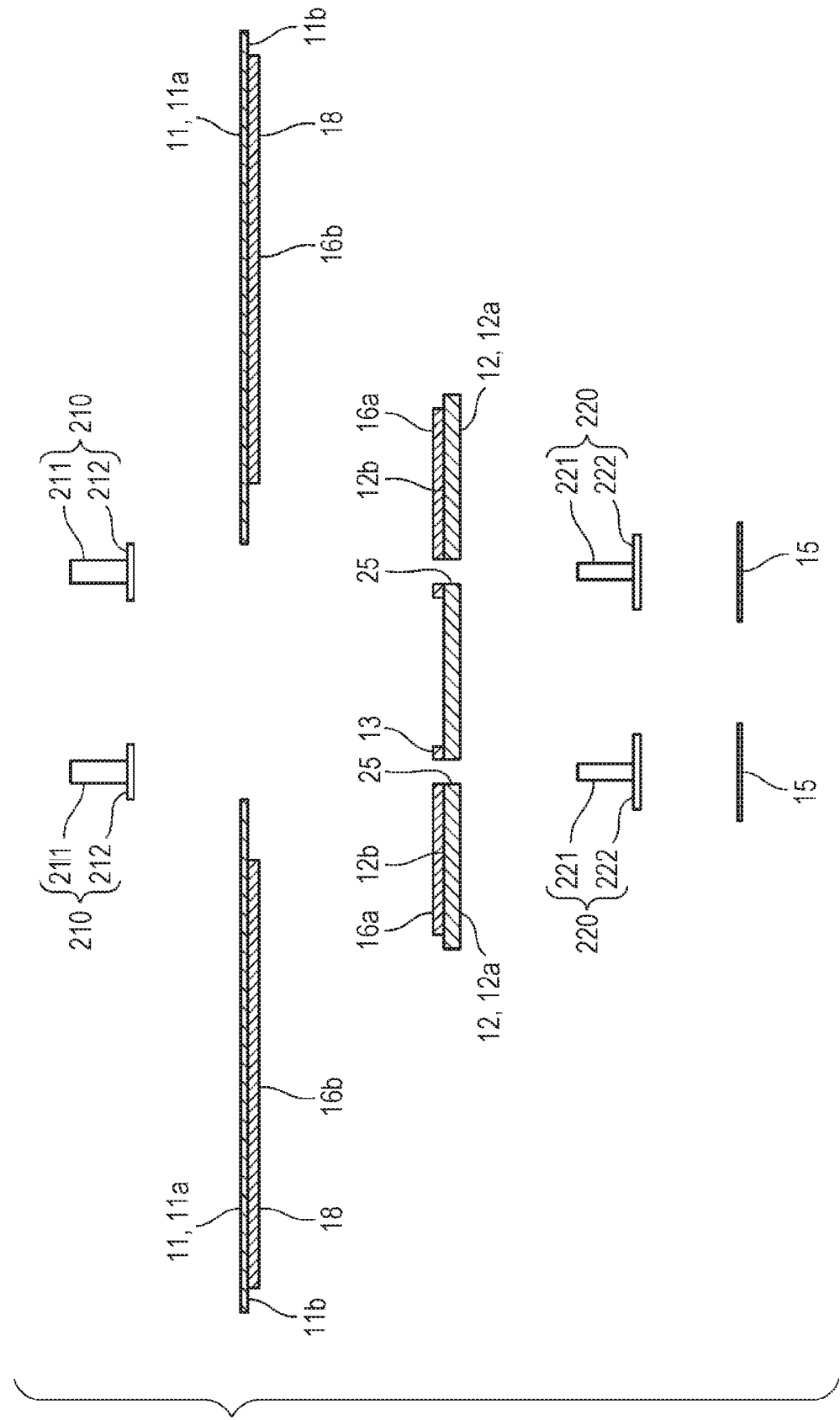
FIG. 4 is an exploded view of the stretchable wiring board illustrated in FIG. 2

FIG. 3 is a top view of the stretchable wiring board 10 illustrated in FIG. 1. FIG. 4 is an exploded view of the stretchable wiring board 10 illustrated in FIG. 2. As illustrated in FIGS. 2 and 3, the wiring electrode 13 is formed on the lower surface 11b of the base material 11 together with the wiring line 16 following the wiring electrode 13. At an end of the wiring electrode 13, the electrode pad 18 for allowing the current to flow to the skin S is formed in the same process as a part of the wiring line 16. The lower surface 11b of the base material 11 is supported by the non-stretchable base material 12. The non-stretchable base material 12 is bonded to the lower surface 11b of the base material 11 by, for example, a lamination process. Therefore, the stretchable wiring board 10 is formed with a stretchable region As and a non-stretchable region Ans. The stretchable region As does not include the non-stretchable base material 12. On the other hand, the non-stretchable region Ans has little stretchability because of the non-stretchable base material 12.

The conductive hooks 21a and 21b pass through holes 25 formed in the non-stretchable base material 12. Thus, the conductive hooks 21a and 21b are attached to the base material 11. This restrains the base material 11 from cracking. Further, attachment points of the conductive hooks 21a and 21b are stabilized.

In the structure illustrated in FIGS. 3 and 2, a main projecting portion 221 (FIG. 4) passes only through the hole 25 of the non-stretchable base material 12. However, the first embodiment is not limited to such a structure. In the first embodiment, for example, the base material 11 may be present around the hole 25 of the non-stretchable base material 12. That is, in the first embodiment, the base material 11 may have a base material side hole (not shown) overlapping the hole 25 of the non-stretchable base material 12. At this time, a projecting portion 220 projects from the hole of the base material 11 and the base material side hole.

In such a structure, an area for attaching the base material 11 to the non-stretchable base material 12 increases. Further, in this structure, the projecting portion 220 contributes to strengthening bonding between the base material 11 and the non-stretchable base material 12. This structure can improve reliability of the stretchable wiring board 10.

As illustrated in FIGS. 4 and 5, the conductive hooks 21a and 21b include the projecting portion 220 projecting from the hole 25 formed in the non-stretchable base material 12, and a cap portion 210 crimped to the projecting portion 220. The projecting portion 220 has the main projecting portion 221 and a fixing plate 222. Further, the cap portion 210 has a main cap portion 211 into which the main projecting portion 221 is inserted, and an overhanging portion 212 overhanging from an edge of the main cap portion 211. The projecting portion 220 passes through the hole 25 formed in the non-stretchable base material 12 and projects from an upper surface 12b. At this time, the fixing plate 222 having a diameter larger than the diameter of the hole 25 remains under a lower surface 12a of the non-stretchable base material 12 without passing through the hole 25.

The cap portion 210 engages with the projecting portion 220 such that the main projecting portion 221 projecting from the upper surface 12b is inserted into the main cap portion 211. The overhanging portion 212 is supported on the upper surface 12b of the non-stretchable base material 12. At this time, the main cap portion 211 is plastically deformed by pressure from above. Thus, the main projecting portion 221 is plastically deformed together with the main cap portion 211 in the main cap portion 211. By such processing, the cap portion 210 and the projecting portion 220 are fixed to each other. Such a fixing method is hereinafter referred to as "crimping".

Hereinafter, the above structures will be described in order.

(Base Material)

Examples of preferable materials for forming the base material 11 include nitrile rubber, latex rubber, and elastomer materials such as urethane-based elastomers. However, the material of the base material 11 is not limited thereto. Especially when a urethane-based elastomer sheet used for medical purposes is attached to the human skin, high safety can be obtained.

The thickness of the base material 11 is not particularly limited. Preferably, the base material 11 has a thickness of, for example, 100 µm or less from the viewpoint of not hindering expansion and contraction movement of an object (object surface) to which the stretchable wiring board 10 is applied. The base material 11 more preferably has a thickness of 25 µm or less, and still more preferably 10 µm or less.

The base material 11 has stretchability as its characteristic. Due to this stretchability, the base material 11 is stretched when tension acts on the base material 11. Further, the base material 11 contracts in response to a compressive force acting on the base material 11. The base material 11 shows a larger dimensional change when stretched than when it contracts. A maximum elongation rate of the base material 11 is preferably 10% or more, more preferably 50% or more, still more preferably 100% or more, and particularly preferably 200% or more. The base material 11 made of the above-described material can exhibit, for example, a maximum elongation rate of 300% or more. Here, the maximum elongation rate of the base material 11 refers to a maximum value of the elongation rate that allows elastic deformation in one direction in an in-plane direction. In the present embodiment, the elongation rate means a ratio of a dimension elongated in one direction in the in-plane direction due to the applied tension to the dimension when no external force is applied (dimension of elongation rate 0%). For example, if the elongation rate is 50%, the stretched base material 11 has a dimension in a stretching direction 1.5 times the elongation rate of 0%. If the elongation rate is 100%, the stretched base material 11 has a dimension in the stretching direction twice the elongation rate of 0%.

(Non-Stretchable Base Material)

The non-stretchable base material 12 is a member having flexibility. Therefore, the non-stretchable base material 12 has a larger Young's modulus than the base material 11. In the present embodiment, the non-stretchable base material 12 has lower stretchability than the base material 11. The non-stretchable base material 12 is preferably a member that hardly expands or contracts substantially. The material of the non-stretchable base material 12 is not particularly limited. Examples of the non-stretchable base material 12 that can be used include a synthetic resin having low slidability, corrosion resistance and high strength, such as polyethylene terephthalate (PET), polyethylene naphthalate (PEN), polyimide (PI), polyphenylene sulfide (PPS), and fluororesin. In addition, as the non-stretchable base material 12, a paper material having appropriate durability, such as cellulose nanofiber paper may be used.

The thickness of the non-stretchable base material 12 is 10 µm or more and 200 µm or less, preferably 25 µm or more and 150 µm or less, and more preferably 50 µm or more and 100 µm or less. Further, the non-stretchable base material 12 preferably has a larger thickness than the base material 11. When the non-stretchable base material 12 has a thickness in the above range, in-plane rigidity of a region where the conductive hooks 21a and 21b are formed is sufficiently increased. At the same time, the overall thickness of the stretchable wiring board 10 can be suppressed.

(Wiring Line)

The wiring line 16 is a conductive pattern having stretchability connected to the wiring electrode 13. The wiring electrode 13 overlaps a part of the conductive hooks 21a and 21b. The wiring electrode 13 supplies power supplied from the external device 3 to the conductive hooks 21a and 21b to the wiring line 16. Further, the wiring electrode 13 also supplies power to the electrode pad 18 through the wiring line 16.

As illustrated in FIG. 4, the wiring line 16 includes a base material side wiring line 16b coated and formed on the lower surface 11b of the base material 11 and a non-stretchable side wiring line 16a formed on the upper surface 12b of the non-stretchable base material 12. The wiring electrode 13 is connected to an end of the non-stretchable side wiring line 16a, and the non-stretchable wiring line 16a and the wiring electrode 13 are coated and formed at the same time in the same process. Further, the electrode pad 18 is connected to an end of the base material side wiring line 16b, and the base material side wiring line 16b and the electrode pad 18 are coated and formed at the same time in the same process. In this coating process, conductive ink is applied to the lower surface 11b. Specific examples include screen printing and inkjet coating.

Examples of methods used for joining the non-stretchable side wiring line 16a and the base material side wiring line 16b include lamination connection and pressure pressing.

The thickness dimension and the width dimension of the wiring line 16 can be determined by a difference between the resistance of the wiring line 16 when no load is applied to the base material 11 and the resistance of the wiring line 16 when the base material 11 is stretched. In addition to this change in the resistance of the wiring line 16, the thickness dimension and the width dimension of the wiring line 16 can be determined based on restrictions on the overall thickness dimension and the width dimension of the stretchable wiring board 10. From the viewpoint of ensuring good stretchability by following dimensional change when the base material 11 is stretched, the width dimension of the wiring line 16 is preferably 1000 µm or less, more preferably 500 µm or less, and still more preferably 200 µm or less. The thickness dimension of each wiring line 16 may be 25 µm or less, and is preferably 10 µm or more and 15 µm or less. The thickness of the wiring electrode 13 and the electrode pad 18 can be determined in the same manner as the wiring line 16.

(Conductive Hook)

Figure 5A:
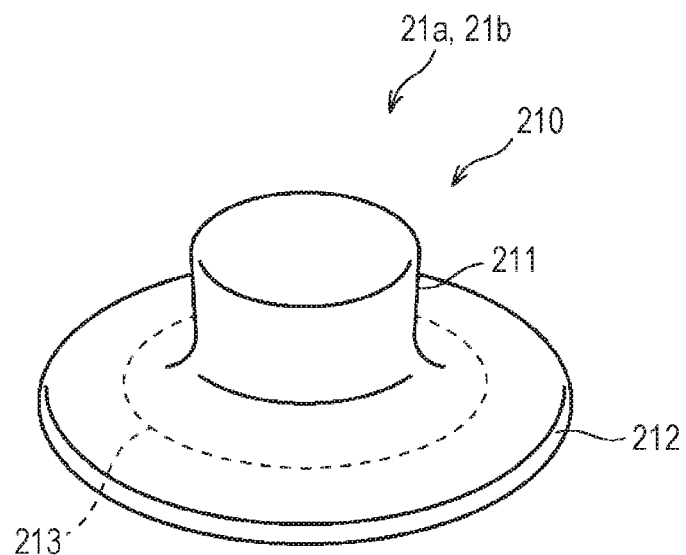
FIG. 5A is a perspective view illustrating a cap portion illustrated in FIG. 4.
Figure 5B:
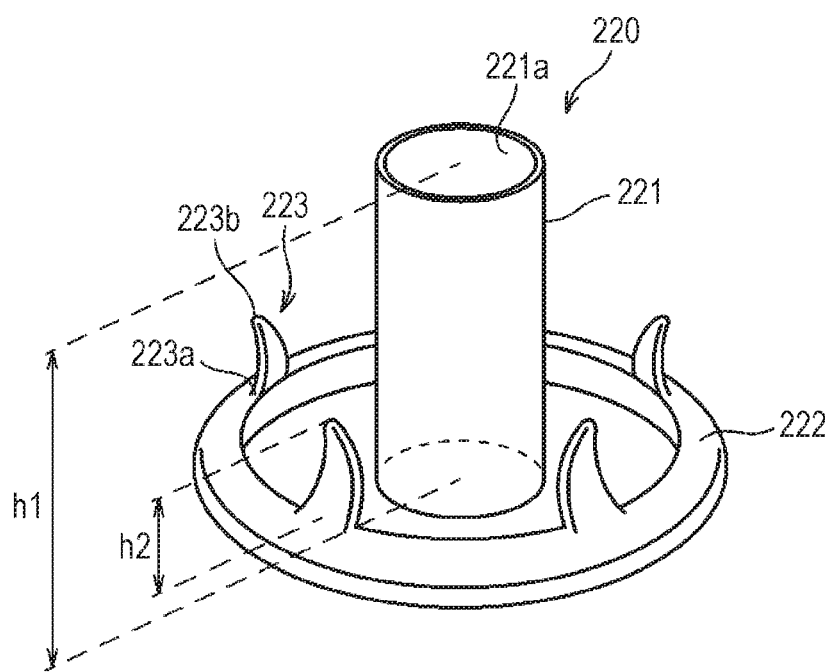
FIG. 5B is a perspective view illustrating a projecting portion.

FIGS. 5A and 5B are perspective views illustrating the cap portion 210 and the projecting portion 220 illustrated in FIG. 4. As illustrated in FIG. 5B, the projecting portion 220 includes the fixing plate 222 and the main projecting portion 221 projecting from the fixing plate 222. A cavity 221a is formed inside the main projecting portion 221.

Although not illustrated in FIG. 4, the projecting portion 220 further includes a plurality of claw projecting portions 223 arranged around the main projecting portion 221. A length h2 of the claw projecting portion 223 in a projecting direction is shorter than a length h1 of the main projecting portion 221 in the projecting direction. Here, the length in the projecting direction refers to a maximum length of each of the main projecting portion 221 and the claw projecting portion 223 in a vertical direction. The length h1 of the main projecting portion 221 in the projecting direction is equal to a height of the columnar main projecting portion 221.

In the projecting portion 220 illustrated in FIG. 5B, an outer edge of the fixing plate 222 is bent toward the center of the fixing plate 222 and stands up. The claw projecting portion 223 is formed on the outer edge of the fixing plate 222 that stands up. The length h2 of the claw projecting portion 223 in the projecting direction is a vertical length from a boundary 223a between a standing-up portion of the fixing plate 222 and the claw projecting portion 223 to a vertex 223b.

Figure 9:
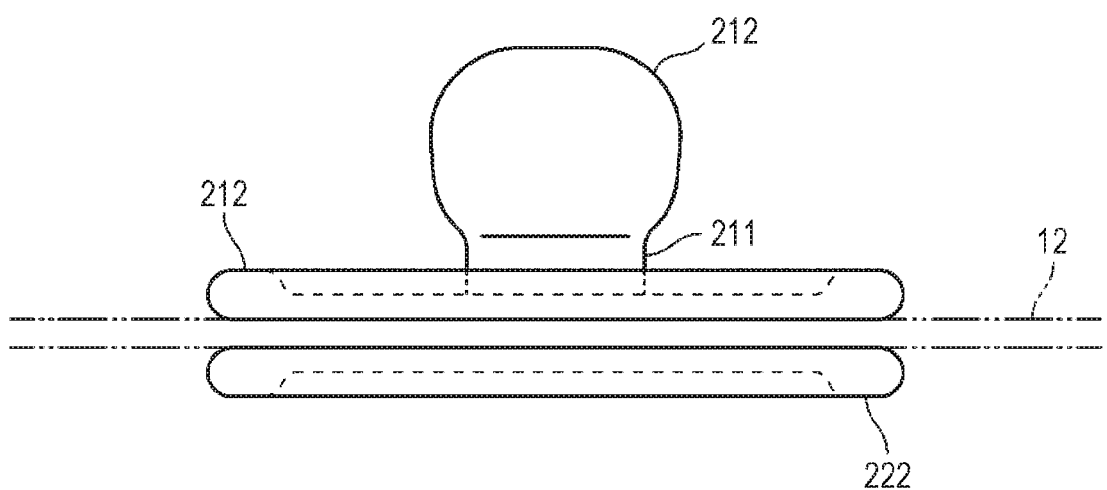
FIG. 9 is a schematic side view illustrating the cap portion and the projecting portion illustrated in FIGS. 6A and 6B after crimping.

That is, in the first embodiment, as illustrated in FIGS. 5A and 5B, in the projecting portion 220 before "crimping", the length h1 of the main projecting portion 221 is longer than the length h2 of the claw projecting portion 223. Note that, as described below, in the first embodiment, even after "crimping", the length of the main projecting portion 221 in the projecting direction is longer than the length of the claw projecting portion 223 in the projecting direction (FIG. 9).

As illustrated in FIG. 5A, the cap portion 210 includes a main cap portion 211 into which the main projecting portion 221 is inserted, and a groove 213 which engages with the claw projecting portion 223 around the main cap portion 211. That is, the cap portion 210 includes the overhanging portion 212 that continues to an opening edge (not shown) of recess of the main cap portion 211. In an example illustrated in FIG. 5A, the overhanging portion 212 has a circular outer edge. The groove 213 is a recessed groove that covers the claw projecting portion 223. Therefore, the groove 213 is located between circumferences of two concentric circles having different diameters. Here, both the concentric circles have diameters smaller than that of the circular outer edge.

From the hole 25, together with the main projecting portion 221 of the projecting portion 220, the claw projecting portion 223 also projects to the upper surface 12b side of the non-stretchable base material 12. Here, the main projecting portion 221 projects from the hole 25 that has been opened in advance. On the other hand, a hole from which the claw projecting portion 223 projects may be opened in advance similarly to the hole 25, or may be separately formed in the non-stretchable base material 12. As described with reference to FIG. 4, the cap portion 210 covers the projecting portion 220. At this time, the groove 213 formed on the edge of the overhanging portion 212 covers the claw projecting portion 223. Then, the cap portion 210 is flatly plastically deformed by the pressure applied to the cap portion 210 by a tool or a press machine. At this time, the main projecting portion 221 is plastically deformed inside the main cap portion 211. At the same time, the claw projecting portion 223 is plastically deformed in the groove 213. After plastic deformation, the cap portion 210 and the projecting portion 220 are firmly connected to each other. Therefore, according to the first embodiment, poor conduction due to the conductive hooks 21a and 21b is suppressed. As a result, the reliability of the stretchable wiring board 10 can be improved.

Further, as described above, the base material 11 of the stretchable wiring board 10 of the first embodiment is attached to a surface of the skin S. Therefore, the fixing plate 222 can be exposed toward the skin S. In the first embodiment, the fixing plate 222 includes the insulating tape 15 as an insulating sheet that prevents electric conduction between the fixing plate 222 and the surface of the skin S (FIGS. 2 and 4).

Figure 6A:
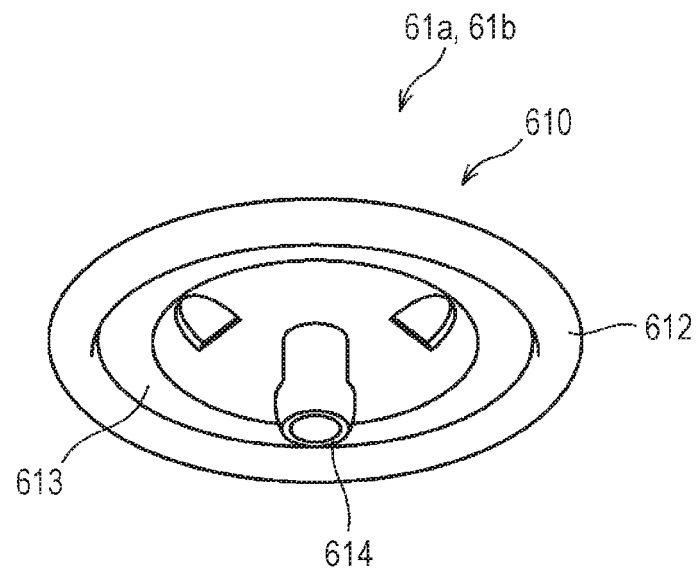
FIG. 6A is a view illustrating a cap portion of a conductive hook having a recess.
Figure 6B:
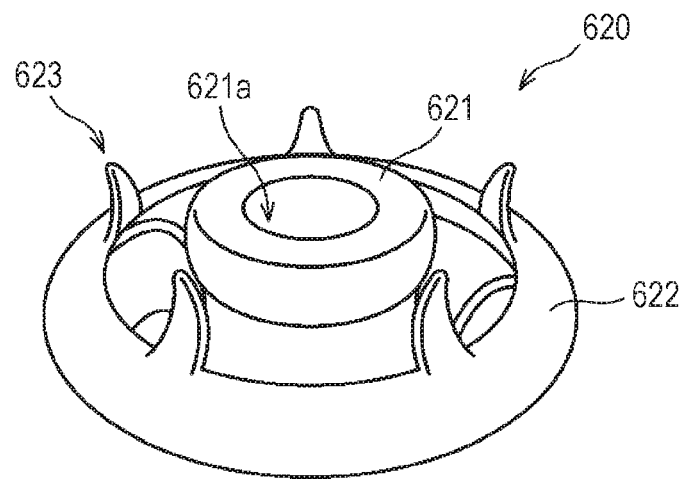
FIG. 6B is a view illustrating a projecting portion.

As illustrated in FIGS. 5A and 5B, the conductive hooks 21a and 21b are not limited to members inserted into the recesses 32a and 32b. For example, when the connection terminals 31a and 31b are configured to project, the conductive hooks 21a and 21b may have recesses into which the connection terminals 31a and 31b are inserted. FIGS. 6A and 6B are views illustrating conductive hooks 61a and 61b having recesses. FIG. 6A is a view showing a cap portion 610. FIG. 6B is a view illustrating a projecting portion 620.

As illustrated in FIG. 6A, the cap portion 610 includes a protrusion 614 and an overhang portion 612 following the protrusion 614. The overhanging portion 612 has a groove 613 formed therein. The groove 613 is a recessed groove that covers a claw projecting portion 623. Therefore, the groove 613 is located between circumferences of two concentric circles having different diameters. Here, both the concentric circles have diameters smaller than that of an outer edge of the overhang portion 612.

As illustrated in FIG. 6B, the projecting portion 620 includes a main projecting portion 621, a fixing plate 622 supporting the main projecting portion 621, and a claw projecting portion 623 formed around the main projecting portion 621. The main projecting portion 621 is formed with a recess 621a into which the protrusion 614 is inserted.

When the conductive hooks 61a and 61b are used, the projecting portion 620 is applied from the side of the upper surface 12b. At this time, the main projecting portion 621 and the claw projecting portion 623 project from the hole 25 formed in the non-stretchable base material 12 toward the lower surface 12a. Then, the cap portion 610 and the projecting portion 620 engage with each other such that the protrusion 614 of the cap portion 610 is inserted into the recess 621a from the side of the lower surface 12a. Subsequently, the both are plastically deformed by the pressure applied to the cap portion 610 and the projecting portion 620. Thus, the both are crimped to each other. As a result, the projecting portion 220 is fixed on the upper surface 12b such that the recessed groove formed between the main projecting portion 621 and the recess 621a faces the external device 3.

In such a case, the connection terminals 31a and 31b formed in a convex shape along the recessed groove are inserted into the recessed groove of the projecting portion 620. Thus, the power can be supplied from the external device 3 to the side of the stretchable wiring board 10.

Figure 7:
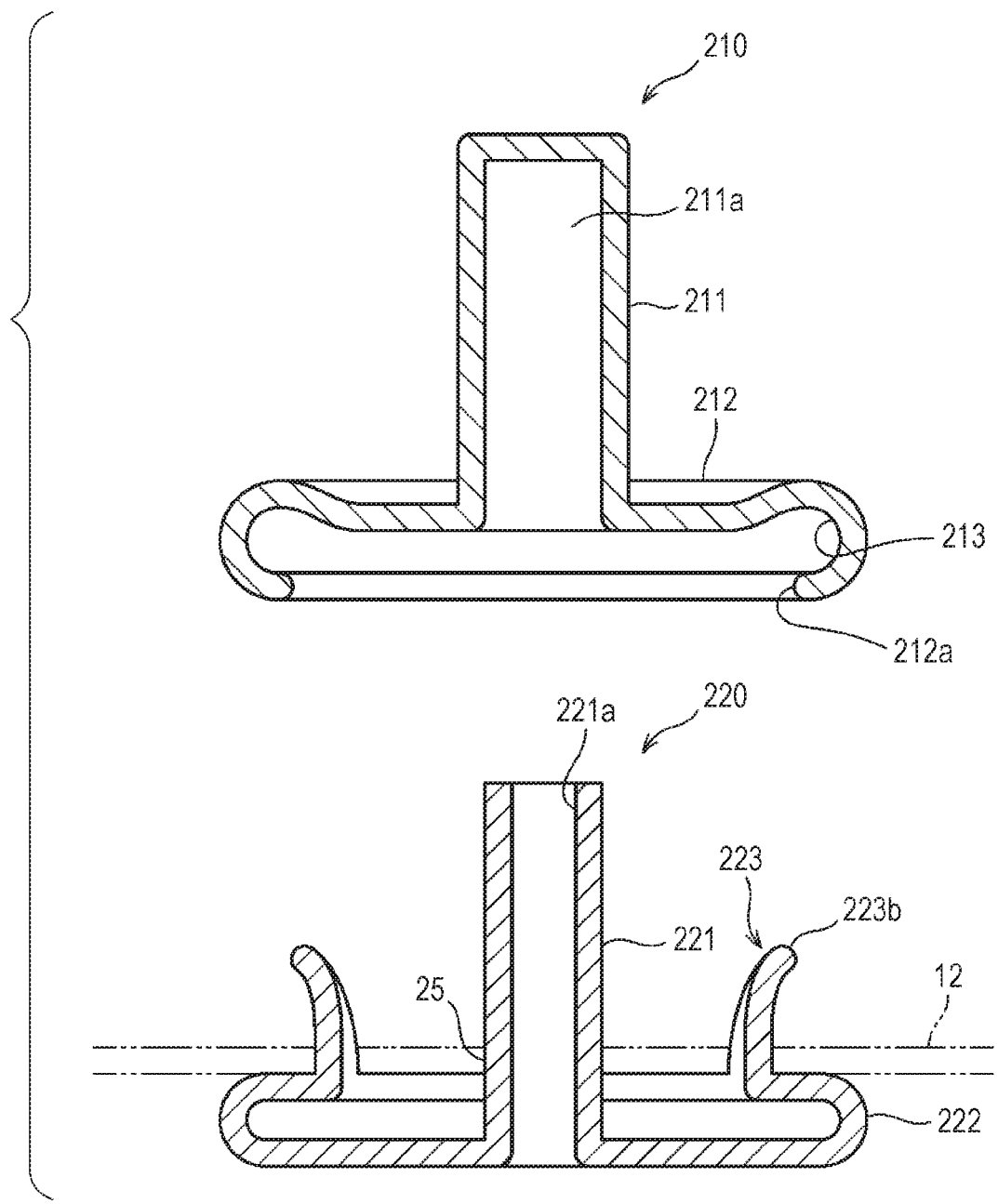
FIG. 7 is a schematic end view illustrating the cap portion and the projecting portion illustrated in FIGS. 6A and 6B before crimping.
Figure 8:
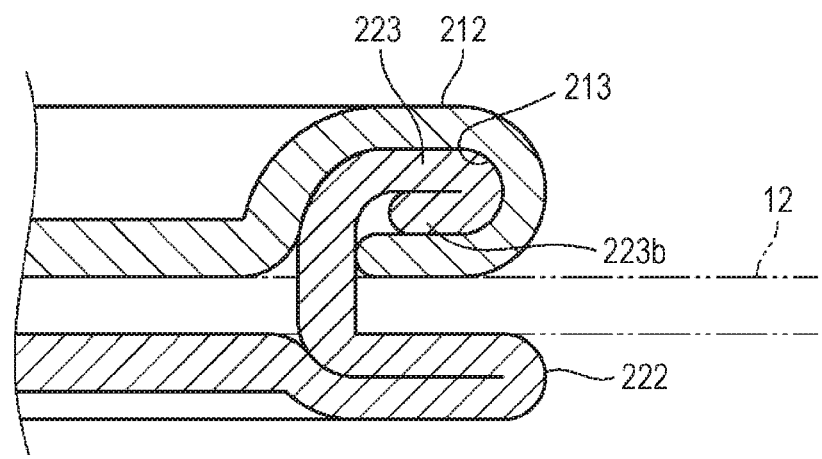
FIG. 8 is a schematic end view illustrating a part of the cap portion and the projecting portion illustrated in FIGS. 6A and 6B after crimping.

FIGS. 7, 8 and 9 are views illustrating cramping the cap portion 210 and the projecting portion 220 illustrated in FIGS. 5A and 5B. FIG. 7 is a schematic end view illustrating the cap portion 210 and the projecting portion 220 before "cramping". FIG. 8 is a schematic end view illustrating a part of the cap portion 210 and the projecting portion 220 after "cramping". FIG. 9 is a schematic side view for explaining the cap portion 210 and the projecting portion 220 after "cramping". FIGS. 7 to 9 illustrate the virtual non-stretchable base material 12 by a two-dot chain line.

As illustrated in FIG. 7, a periphery of the overhang portion 212 is raised compared to the central portion. Then, an outer edge portion 212a is curved and wound toward the center. Therefore, the thickness around the groove 213 is larger than the thickness near the center of the overhanging portion 212.

As is clear from FIG. 7, the vertex 223b of the claw projecting portion 223 of the projecting portion 220 is slightly warped outward (toward the outer edge of the fixing plate 222). With such a shape, when the cap portion 210 is covered on the projecting portion 220, the vertex 223b is inserted into the groove 213. At this time, the main projecting portion 221 is inserted into the main cap portion 211.

However, the insertion depth of the main projecting portion 221 into the main cap portion 211 at this time is limited by the insertion depth of the vertex 223b into the groove 213.

Thereafter, the cap portion 210 is fixed by, for example, a jig having a recess (not shown) at the main cap portion 211. At this time, the pressure is applied to the main cap portion 211 and the cap portion 210 from above the jig. Due to the applied pressure, the vertex 223b that is warped outward is further bent outward in the groove 213. As a result, the vertex 223b is engaged with and integrated with the overhanging portion 212 which is also crushed by being pressurized.

In the first embodiment, as illustrated in FIG. 8, the claw projecting portion 223 is bent toward the outer edge of the fixing plate 222 inside the groove 213. At this time, the vertex 223b of the claw projecting portion 223 is bent outward inside the groove 213, and the vertex 233b is folded back to be located below a lower portion of the claw projecting portion 223. The claw projecting portion 223 is crushed inside the groove 213 and is covered by the overhanging portion 212. Therefore, the claw projecting portion 223 does not deform in a direction where it stands up again due to its rigidity. As a result, the projecting portion 220 is firmly fixed to the cap portion 210.

At this time, the main projecting portion 221 having the cavity 221a is crushed inside the main cap portion 211 by being pressurized. The main cap portion 211 has the cavity 211a into which the main projecting portion 221 is inserted, and is formed of a relatively thin metal. Therefore, similarly to the main projecting portion 221, the main cap portion 211 is also plastically deformed so as to be crushed in a pressing direction. As a result, upper portions of the cap portion 210 and the projecting portion 220 have larger diameters than lower portions thereof, as illustrated in FIG. 9. That is, the cap portion 210 and the projecting portion 220 have a rounded convex shape.

The cap portion 210 and the projecting portion 220 of the conductive hooks 21a and 21b thus formed are not released from fixation again. Therefore, the conductive hooks 21a and 21b are firmly attached to the non-stretchable base material 12. With such a structure, it is possible to reduce a possibility of poor connection between the conductive hooks 21a, 21b and the wiring electrode 13 in the stretchable wiring board 10. Also, the reliability of the stretchable wiring board 10 can be improved.

Figure 10:
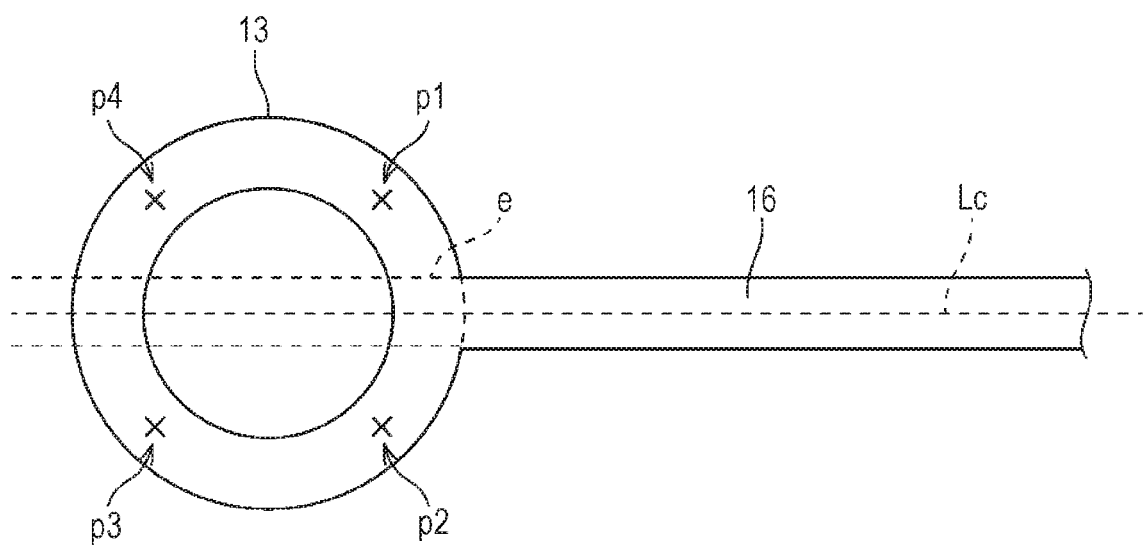
FIG. 10 is a schematic view illustrating a positional relationship between a wiring electrode and a claw projecting portion used in the first embodiment.

FIG. 10 is a schematic view illustrating a positional relationship between the wiring electrode 13 and the claw projecting portion.

Any of the conductive hooks 21a and 21b illustrated in FIGS. 5A and 5B and the conductive hooks 61a and 61b illustrated in FIGS. 6A and 6B have claw projecting portions. Therefore, the projecting portions 220 and 620 and the cap portions 210 and 610 are crimped at two places of the claw projecting portion and the main projecting portion. According to such a structure, the projecting portion and the cap portion can be more firmly fixed than a structure in which the projecting portion and the cap portion are crimped at only one position of the main projecting portion. However, if excessive pressure acts on the claw projecting portion when applying the pressure to the projecting portion and the cap portion, a crack may be formed in the wiring electrode 13 below the claw projecting portion or the wiring line 16 connected to the wiring electrode 13.

In consideration of the above points, in the first embodiment, by appropriately designing the conductive hook (referred to as the conductive hook 21a), as illustrated in FIG. 10, the claw projecting portion is arranged at a position that does not interfere with at least a part of an imaginary extension region e on an extension of the wiring line 16 on the wiring electrode 13. In an example illustrated in FIG. 10, the claw projecting portions 223 of the conductive hooks are arranged at positions p1, p2, p3 and p4 so as not to interfere with any part of the extension region e.

Such an arrangement can be realized, for example, by the following method. First, a mark indicating a preferred attachment direction of the conductive hooks 21a and 21b is attached to the cap portion 210 in advance. Subsequently, an operator sets the mark in a predetermined direction and crimps the cap portion 210 and the projecting portion 220.

In the first embodiment, the claw projecting portion 223 may not be disposed at a position that does not interfere with any part of the extension region e. However, the claw projecting portion 223 is preferably disposed at a position that does not interfere with at least a position where a center line Lc of the wiring line 16 passes. In this way, even if a strong local pressure is applied below the claw projecting portion 223, a possibility that the wiring line 16 is cracked is reduced. In addition, it is possible to suppress poor conduction of the stretchable wiring board 10. Note that the wiring electrode 13 is formed to surround a periphery of the conductive hook 21a. Therefore, even if a part of the wiring electrode 13 is cracked, the poor conduction is unlikely to occur.

However, in the first embodiment, the conductive hook is not limited to the structure illustrated in FIGS. 5A to 6B. The conductive hook only needs to have at least a protrusion or a recess that can be electrically connected to the connection terminals 31a and 31b of the external device 3, and be connectable to the wiring line 16 from a plurality of directions around the conductive hook.

Figure 11:
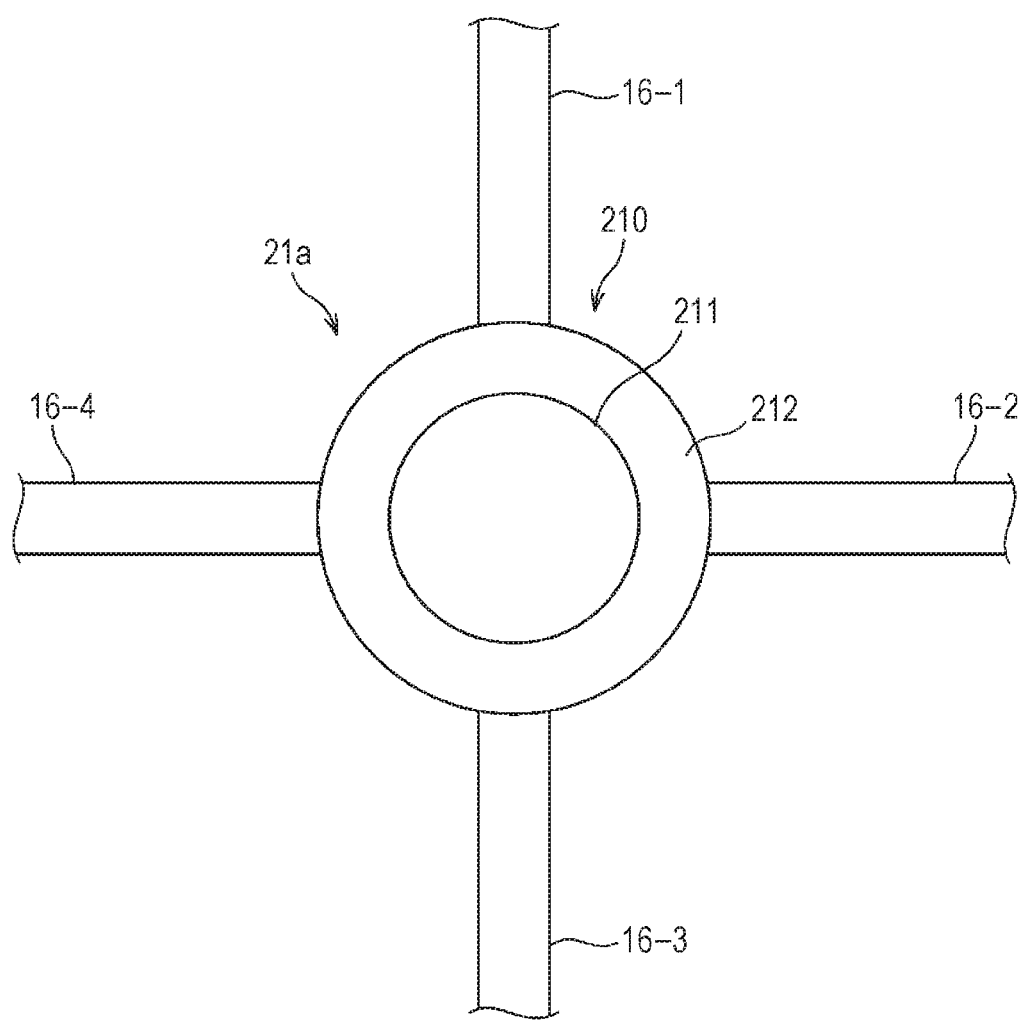
FIG. 11 is a view illustrating effects of the first embodiment in which electric power is supplied from an external device using the conductive hook.

FIG. 1 is a view illustrating effects of the first embodiment in which the power is supplied from the external device 3 using the conductive hook. FIG. 11 is a top view illustrating the conductive hook 21a capable of supplying power to the four wiring lines 16-1, 16-2, 16-3, and 16-4. The conductive hook can supply power to the wiring line 16 by making electrical contact with the wiring line 16. Therefore, the conductive hook has a higher degree of freedom of wiring layout as compared to a connector with restricted wiring insertion/removal direction. For example, when the conductive hook 21a illustrated in FIG. 11 is formed at a center of a circuit, the wiring lines 16 can be connected to the conductive hook 21a from all directions around the conductive hook 21a.

In the structure illustrated in FIG. 11, one wiring electrode 13 preliminarily forms a wiring pattern in which the wiring lines 16-1 to 16-4 extend. The main cap portion 211 is inserted into a through-hole formed in the wiring electrode 13. Then, the main cap portion 211 and the cap portion 210 are crimped. This can form the structure of FIG. 11.

According to the above structure, the wiring line in the EMS device 1 can be easily multi-channeled.

Second Embodiment

Next, the stretchable wiring board of the second embodiment will be described.

FIGS. 12A and 12B are views illustrating a stretchable wiring board 20 of the second embodiment. FIG. 12A is a top view of the stretchable wiring board 20. FIG. 12B is an end view of a cross-section of the stretchable wiring board 20 taken along a one-dot chain line illustrated in FIG. 12A, as viewed in a direction of arrow lines XIIb and XIIb. In the stretchable wiring board 20, similarly to the stretchable wiring board 10 of the first embodiment, the electrode pad 18 and a part of the wiring line 16 are formed on the lower surface of the base material 11. On the upper surface of the non-stretchable base material 12, the wiring electrode 13 and another portion of the wiring line 16 are formed. Further, the stretchable wiring board 20 includes the conductive hooks 21a and 21b on the non-stretchable base material 12, similarly to the stretchable wiring board 10.

However, the stretchable wiring board 20 is different from the first embodiment in that the non-stretchable base material 12 includes a plurality of non-stretchable base material pieces 12c and 12d. That is, the stretchable wiring board 20 of the second embodiment includes the non-stretchable base material pieces 12c and 12d. Then, a separation space D exists between the non-stretchable base material pieces 12c and 12d. The non-stretchable base material pieces 12c and 12d are respectively joined to base material pieces 11c and 11d. Further, the conductive hooks 21a and 21b are inserted into the recesses 32a and 32b of the external device 3. Thus, an interval between the non-stretchable base material pieces 12c and 12d is fixed.

In the second embodiment, in the stretchable wiring board 20, a portion of the stretchable wiring board 20 having the non-stretchable base material piece 12c and the base material piece 11c is referred to as a stretchable wiring board piece 20c. A portion of the stretchable wiring board 20 having the non-stretchable base material piece 12d and the base material piece 11d is referred to as a stretchable wiring board piece 20d. In the second embodiment, each of the base material piece 11c (stretchable wiring board piece 20c) and the base material piece 11d (stretchable wiring board piece 20d) can be independently attached to the skin S. Therefore, their attachment positions can be easily finely adjusted.

In the stretchable wiring board pieces 20c and 20d illustrated in FIGS. 12A and 12B, the conductive hooks 21a and 21b respectively correspond to the non-stretchable base material pieces 12c and 12d. Therefore, each of the stretchable wiring board pieces 20c and 20d can independently receive power supply from the external device 3. Specifically, in the structure of FIGS. 12A and 12B, the stretchable wiring board piece 20c includes one conductive hook 21a, and the stretchable wiring board piece 20d includes one conductive hook 21b. Thus, the stretchable wiring board 20 can be configured so that the stretchable wiring board pieces 20c and 20d can rotate with respect to the external device 3. At this time, in the second embodiment, the stretchable wiring board pieces 20c and 20d can be attached to the external device 3 at arbitrary angles. According to the second embodiment, an attachment angle of the stretchable wiring board pieces 20c and 20d can be appropriately changed depending on a shape of a portion of the body where the stretchable wiring board 20 is to be applied. Thus, the shape of the EMS device 1 can be arbitrarily changed.

FIGS. 13A and 13B are diagrams illustrating a stretchable wiring board 30 of a modification of the second embodiment. FIG. 13A is a top view of the stretchable wiring board 30. FIG. 13B is an end view of a cross-section of the stretchable wiring board 30 taken along a one-dot chain line illustrated in FIG. 13A, as viewed in a direction of arrow lines XIIIb and XIIIb.

The stretchable wiring board 30 is different from the stretchable wiring board 20 in that the base material 11 connects the non-stretchable base material piece 12c and the non-stretchable base material piece 12d. When the stretchable wiring board 30 of the modification is compared with the stretchable wiring board 20, there is the base material 11 between the non-stretchable base material piece 12c and the non-stretchable base material piece 12d. Therefore, the same adhesiveness to the skin S as the stretchable wiring board 10 of the first embodiment can be obtained. The non-stretchable base material is separated into the non-stretchable base material piece 12c and the non-stretchable base material piece 12d. Therefore, the attachment positions of the base material pieces 11c and 11d can be finely adjusted more easily than the stretchable wiring board 10.

The above embodiments include the following technical concept.

(1) A stretchable wiring board including: a base material having stretchability; a wiring line having at least a portion coated and formed on the base material with a conductive stretchable material; and an uneven engaging portion that is electrically connected to the wiring line and has a protrusion or a recess engaging with a connection terminal of an external device.

(2) The stretchable wiring board according to (1), further including a non-stretchable base material provided on one side of the base material and supporting the base material.

(3) The stretchable wiring board according to (2), wherein the non-stretchable base material includes a plurality of non-stretchable base material pieces.

(4) The stretchable wiring board according to any one of (1) to (3), wherein the uneven engaging portion includes a projecting portion projecting from a hole formed in the non-stretchable base material, and a cap portion crimped to the projecting portion.

(5) The stretchable wiring board according to (3), wherein the uneven engaging portion is provided corresponding to each of the non-stretchable base material pieces, and connects the non-stretchable base material piece to the external device at an arbitrary angle.

(6) The stretchable wiring board according to (4) or (5), wherein the base material is present around the hole of the non-stretchable base material.

(7) The stretchable wiring board according to any one of (3) to (6), wherein the base material connects the non-stretchable base material pieces.

(8) The stretchable wiring board according to any one of (1) to (7), wherein the uneven engaging portion includes a projecting portion, and a cap portion crimped to the projecting portion, the projecting portion includes a fixing plate, a main projecting portion projecting from the fixing plate, and a plurality of claw projecting portions having a length in a projecting direction shorter than that of the main projecting portion and formed around the main projecting portion, and the cap portion includes a main cap portion into which the main projecting portion is inserted, and a groove engaged with the claw projecting portion around the main cap portion.

(9) The stretchable wiring board according to (8), wherein the fixing plate includes an insulating sheet that prevents electric conduction.

(10) The stretchable wiring board according to (8) or (9), wherein in the uneven engaging portion, the claw projecting portion is disposed to be located at a position excluding at least a part of a virtual extension region on an extension of the wiring line.

(11) An electrical muscle stimulating device including: a stretchable wiring board including a base material having stretchability, a wiring line coated and formed on the base material with a conductive stretchable material, and an uneven engaging portion electrically connected to the wiring line and having a protrusion or a recess; and an external device including a connection terminal engaged with the protrusion or the recess of the uneven engaging portion.

What is claimed is:

1. A stretchable wiring board comprising:
    a base material having stretchability;
    a wiring line having at least a portion coated and formed on the base material with a conductive stretchable material; and
    an uneven engaging portion that is electrically connected to the wiring line and has a protrusion or a recess configured to engage with a connection terminal of an external device, wherein
    the base material has a first side and a second side opposite to the first side,
    the wiring line is disposed on the first side of the base material, and
    the second side of the base material faces the connection terminal of the external device.

2. The stretchable wiring board according to claim 1, further comprising a non-stretchable base material disposed on the first side of the base material and supporting the base material.

3. The stretchable wiring board according to claim 2, wherein the non-stretchable base material comprises a plurality of non-stretchable base material pieces.

4. The stretchable wiring board according to claim 2, wherein the uneven engaging portion comprises a projecting portion projecting from a hole formed in the non-stretchable base material, and a cap portion crimped to the projecting portion.

5. The stretchable wiring board according to claim 3, wherein the uneven engaging portion corresponds to each of the non-stretchable base material pieces, and is configured to connect the non-stretchable base material piece to the external device at an arbitrary angle.

6. The stretchable wiring board according to claim 4, wherein the base material is present around the hole of the non-stretchable base material.

7. The stretchable wiring board according to claim 3, wherein the base material connects the non-stretchable base material pieces.

8. The stretchable wiring board according to claim 1, wherein
    the uneven engaging portion comprises a projecting portion, and a cap portion crimped to the projecting portion,
    the projecting portion comprises a fixing plate, a main projecting portion projecting from the fixing plate, and a plurality of claw projecting portions having a length in a projecting direction shorter than that of the main projecting portion and formed around the main projecting portion, and
    the cap portion comprises a main cap portion into which the main projecting portion is inserted, and a groove engaged with the claw projecting portion around the main cap portion.

9. The stretchable wiring board according to claim 8, wherein the fixing plate comprises an insulating sheet that prevents electric conduction.

10. The stretchable wiring board according to claim 8, wherein the uneven engaging portion comprises the claw projecting portion disposed at a position that does not interfere with at least a part of a virtual extension region on an extension of the wiring line.

11. An electrical muscle stimulating device comprising:
    a stretchable wiring board comprising a base material having stretchability, a wiring line coated and formed on the base material with a conductive stretchable material, and an uneven engaging portion electrically connected to the wiring line and having a protrusion or a recess; and an external device comprising a connection terminal engaged with the protrusion or the recess of the uneven engaging portion, wherein the base material has a first side and a second side opposite to the first side, the wiring line is disposed on the first side of the base material, and the second side of the base material faces the connection terminal of the external device.

12. The stretchable wiring board according to claim 1, wherein the uneven engaging portion protrudes from the second side of the base material.

* * * * *